United States Patent [19]

Candela et al.

[11] Patent Number: 4,950,794

[45] Date of Patent: Aug. 21, 1990

[54] ETHYLBENZENE OXIDATION

[75] Inventors: Lawrence M. Candela, Philadelphia; Robert N. Cochran, West Chester, both of Pa.; Scott H. Sandler, Peabody, Mass.

[73] Assignee: Arco Chemical Technology, Inc., Wilmington, Del.

[21] Appl. No.: 356,081

[22] Filed: May 24, 1989

[51] Int. Cl.$^5$ ............................................. C07C 45/33
[52] U.S. Cl. .................................. 568/320; 568/569; 568/574; 568/798; 568/802
[58] Field of Search .......................... 568/320, 569, 574

[56] References Cited

U.S. PATENT DOCUMENTS

| | | | |
|---|---|---|---|
| 2,632,772 | 3/1953 | Armstrong et al. | 568/569 |
| 2,867,666 | 1/1959 | Erickson et al. | 568/320 |
| 3,592,857 | 7/1971 | Shinohara | 568/320 |
| 4,066,706 | 1/1978 | Schmidt | 568/569 |
| 4,262,143 | 4/1981 | Becker | 568/574 |
| 4,329,514 | 5/1982 | van der Weijst et al. | 568/569 |

FOREIGN PATENT DOCUMENTS

| | | | |
|---|---|---|---|
| 4314449 | of 0000 | Japan | 568/569 |
| 1330128 | 8/1987 | U.S.S.R. | 568/320 |

*Primary Examiner*—James H. Reamer
*Attorney, Agent, or Firm*—Long, William C.

[57] ABSTRACT

The oxidation of ethylbenzene to products comprised of ethylbenzene hydroperoxide and acetophenone is modified in order to enhance acetophenone production by reducing the alkali content of the oxidation mixture below 0.1 ppm and by incorporation of 0.05 to 2 wt. % water in the oxidation mixture.

2 Claims, 5 Drawing Sheets

ETHYLBENZENE OXIDATION

BACKGROUND OF THE INVENTION

1. Field of the Invention

The present invention relates to the oxidation of ethylbenzene to form products comprised of ethylbenzene hydroperoxide and acetophenone. In particular, the invention provides a method for increasing the amount of acetophenone which is formed relative to ethylbenzene hydroperoxide by reducing the alkali metal content of the ethylbenzene oxidation reaction mixture to below 0.1 ppm and by incorporating small amounts of water in the reaction mixture.

2. Description of the Prior Art

The oxidation of ethylbenzene to form products comprised of ethylbenze hydroperoxide is a known reaction which is practiced commercially in the coproduction of propylene oxide and styrene monomer. Ethylbenzene hyroperoxide thus formed is reacted with propylene to form propylene oxide with the hydroperoxide mainly being converted to methyl benzyl alcohol; some acetophenone is formed in this step as well as in the ethylbenzene oxidation step. Generally, the acetophenone is hydrogenated to methyl benzyl alcohol and such methyl benzyl alcohol, together with that formed by reaction of the hydroperoxide with the olefin, is dehydrated to the styrene monomer coproduct. U.S. Pat. No. 3,351,635 is illustrative of this technology.

U.S. Pat. No. 3,439,001 teaches that recycle ethylbenzene in the above process is advantageously treated with alkali in order to avoid residue formation during the propylene epoxidation. The treated ethylbenzene is desirably washed to remove residual alkali.

U.S. Pat. No. 4,066,706 provides a method for oxidizing ethylbenzene to the hydroperoxide whereby temperature of reaction is decreased in the direction of flow.

U.S. Pat. No. 2,867,666 teaches the oxidation of ethylbenzene to ethylbenzene hydroperoxide and stresses that the reaction should be carried out under anhydrous conditions and that the presence of basic material is critical.

U.S. Pat. No. 2,592,857 takes issue with the above and provides data (Table III) showing that acetophenone make increases and ethylbenzene hydroperoxide make decreases with the addition of increasing amounts of alkali.

Japanese patent publication 43-14449 which is by the same inventor as U.S. Pat. No. 3,592,857, carries out ethylbenzene oxidation to ethylbenzene hydroperoxide in the presence of small amounts of water, i.e., 0.5 to 2% by weight. Runs both with and without added alkali are described. Alkali is described as useful in preventing acids which are formed during oxidation from acting to decompose hydroperoxide or from inhibiting oxidation. The data suggest that water addition decreases ethylbenzene oxidation rate.

U.S. Pat. No. 4,262,143 describes the preparation of ethylbenzene hydroperoxide by oxidizing ethylbenzene in the presence of small but critical amounts of sodium or potassium hydroxide or salt, i.e., 0.1 to 20 ppm of sodium or 0.17 to 34 ppm of potassium whereby rates and selectivities to the hydroperoxide are improved.

During practice of the process for the co-production of propylene oxide and styrene monomer, frequently it is advantageous to be able to quickly and conveniently vary the ratio of the main products in accordance with market variations. The present invention provides a method whereby this variation can be accomplished without the necessity for severe changes in processing procedures and without the necessity for major capital equipment changes.

BRIEF DESCRIPTION OF THE INVENTION

Generally speaking, the molecular oxygen oxidation of ethylbenzene to form ethylbenzene hydroperoxide-containing reaction product mixtures is carried out in the presence of small amounts of alkali such as sodium carbonate, sodium hydroxide, sodium pyrophosphate, and the like. At conventional alkali levels, it has been found that the addition of small amounts of water to the reaction system increases the rate at which ethylbenzene oxidation takes place but has little effect on oxidation product distribution.

In accordance with the present invention, however, there is provided a method by which the ethylbenzene oxidation product distribution can be significantly changed to favor acetophenone production at the expense of ethylbenzene hydroperoxide production without a significant adverse effect on ethylbenzene oxidation rate. Specifically, according to the invention, the alkali content of the ethylbenzene oxidation reaction mixture is reduced from the normal value which is in excess of 0.5 ppm, and usually in excess of 1 ppm by weight expressed as sodium, to below 0.1 ppm while at the samt time the water content of the reaction mixture is controlled in the range 0.5 to 2% by weight.

The objectives of the present invention are two-fold; that is, to adjust the product distribution such that more acetophenone is formed relative to ethylbenzene hydroperoxide while at the same time maintaining a high rate of ethylbenzene conversion. In accordance with the invention, this is accomplished by reducing the level of alkali in the ethylbenzene oxidation mixture from normal values to less than 0.1 ppm alkali while at the same time incorporating small amounts of water in the range 0.5 to 2 wt. % in the oxidation mixture.

DETAILED DESCRIPTION OF THE INVENTION

Figure 1:
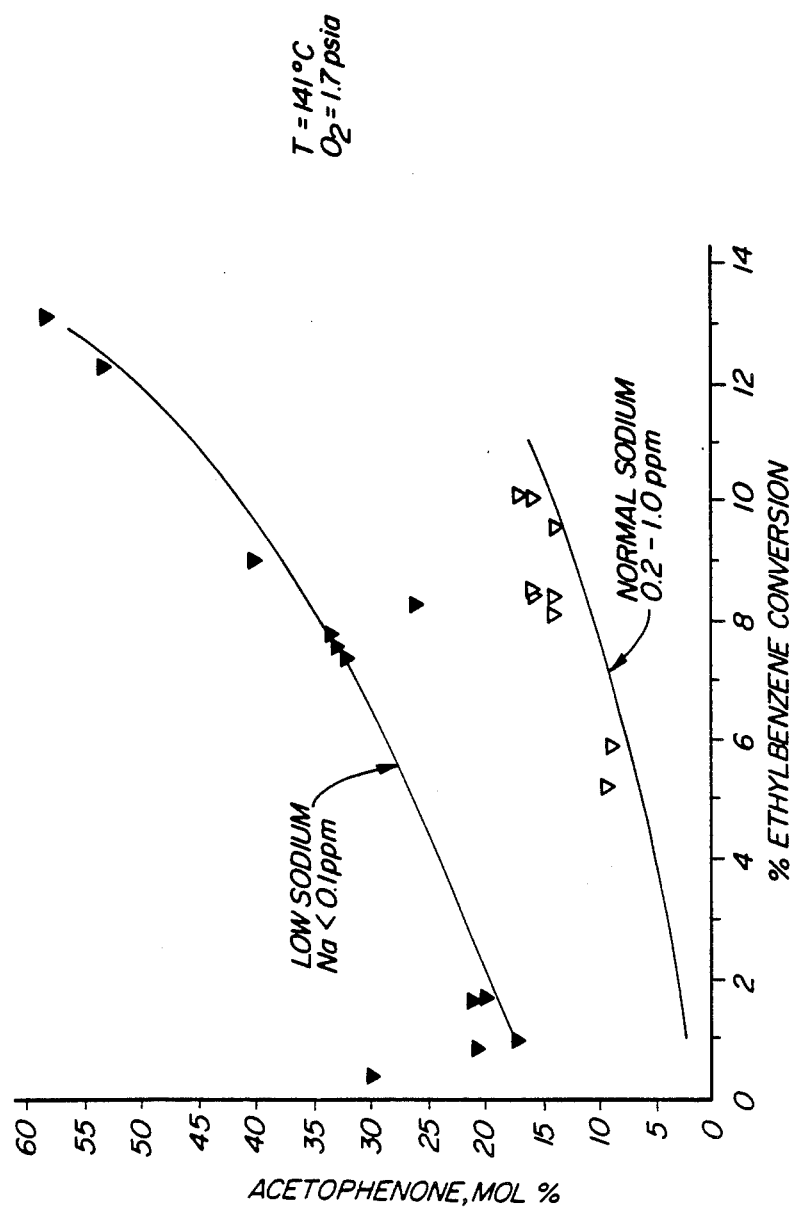
FIG. 1 is a plot of reaction selectivity to acetophenone versus ethylbenzene conversion at various sodium levels.

The process of this invention is not limited to any particular oxidation procedure for the production of hydroperoxides using molecular oxygen, i.e., so-called "auto oxidation". The oxidation can be effected in any standard equipment suitable for oxidation reactions, and the oxidation can be carried out batch-wise or continuously with equal facility, the formation of the hydroperoxides is normally brought about within certain parameters of temperature, pressure and the like and the invention will be more easily understood by describing it in connection with typical operating conditions and with respect to typical reactants and material handling procedures.

For example, any oxygen-bearing gas may be used in this process providing that the gases other than oxygen are inert at the reaction conditions. Air is the preferred oxidation gas because of its ready availability but gases richer or poorer in oxygen than air may be used.

The amount of ethylbenzene that should be converted to any oxidation depends upon several competing factors. As the conversion is increased above 20% of the feed ethylbenzene, the amoutn of by-product increases rapidly and the yield of hydroperoxide is consequently decreased. When the conversion is less than about 5%, the cost of oxidizing a unit amount of ethylbenzene is greatly increased due to the requirements of additional ethylbenzene recycle.

The temperatures at which the ethylbenzene is oxidized are about 120° to 170° C., the preferred range is about 130° to 160° C., and it is most desirable to operate in the range of about 135° to 160° C. At temperatures lower than 120° C., the rate of reaction is undesirably low and temperatures in excess of 170° C. have an adverse effect upon selectivity. The oxidation reaction can be carried out at constant temperature or under programmed temperature conditions as described in U.S. Pat. No. 4,066,706. The formation of by-products can be minimized by optimization of oxygen concentration and mass transfer in accordance with established procedures.

The reaction pressure may be maintained at from about atmospheric to 1000 p.s.i.g., although the pressure is desirably maintained at from 10 p.s.i.g. to 200 p.s.i.g. The oxidation of ethylbenzene is exothermic and it is, of course, necessary that some heat be removed. Heat can be removed by vaporization of oxidate. The total flow of oxidizing gas feed plus recycle gas is adjusted to maintain the desired reaction temperature at the set reactor pressure.

The time required to convert the desired quantity of ethylbenzene is in the range of from ½ to 20 hours depending upon the temperature maintained in the reactor and the oxygen partial pressure.

Generally speaking, for most of the time the oxidation of ethylbenzene is carried out continuously using small amounts of added alkali as provided in U.S. Pat. No. 4,262,143 in order to maximize productin of hydroperoxide which in turn is used in olefin epoxidation. However, there are times when market conditions are such that for best economics it is desirable to produce more acetophenone relative to ethylbenzene hydroperoxide, and the present invention provides a convenient method where this can be accomplished without disrupting the ethylbenzene oxidation system.

In accordance with the invention, the amount of alkali fed to the ethylbenzene oxidation is lowered in order to reduce the alkali content of the oxidation reaction mixture below 0.1 ppm. At the same time, the water content of the reaction mixture is adjusted to 0.05 to 2 wt. %. In this way, high rates of ethylbenzene oxidation are sustained while substantially enhanced production of acetophenone relative to ethylbenzene hydroperoxide is achieved. Methyl benzyl alcohol production is not substantially changed. The water content of the reaction mixture is adjusted by the addition of appropriate amounts of water or by control of reaction conditions to maintain water of reaction in the mixture at the desired concentration, or by a combination of these procedures.

Experiments in continuous oxidation of ethylbenzene were performed in a single-stage, well-mixed autoclave reactor. This system was equipped with temperature, pressure and level controls, as well as controllable ethylbenzene and water feeds. Air/nitrogen was feed sparged in at the base of the reactor and quenched non-condensable off-gases were analyzed for oxygen content. Sodium entered either via caustic injection (with the water feed) or by pretreating the inside of the reactor with sodium pyrophosphate. Sodium removal was performed by vigorous flushing of the system with boiling distilled water for several hours.

Ethylbenzene conversions werre tested from 0.5 to 13% at 141° C. and a total pressure of 35 psig. Oxygen breakthrough was maintained at 5 mole % in the fully non-oxygen-starved regime. The sodium levels tested were 1.0, 0.5, 0.2 and less than 0.1 ppm. The water injection rate was varied to give a range of oxidate water concentrations from 500 to 18000 ppm. The data obtained are presented graphically in FIG. 1-5.

Figure 2:
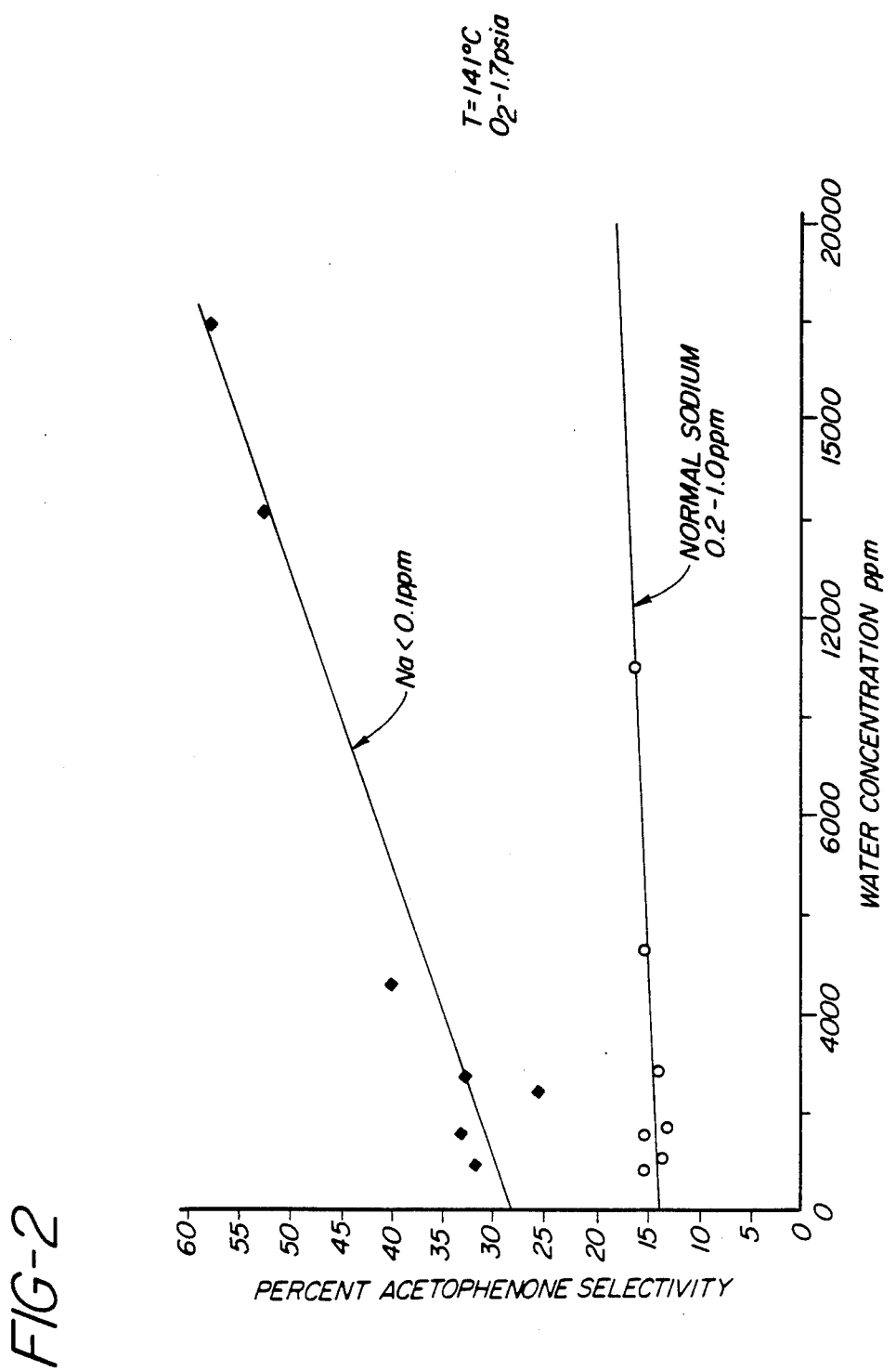
FIG. 2 is a plot of reaction selectivity to acetophenone versus water concentration at high ethylbenzene conversion at various sodium levels.
Figure 3:
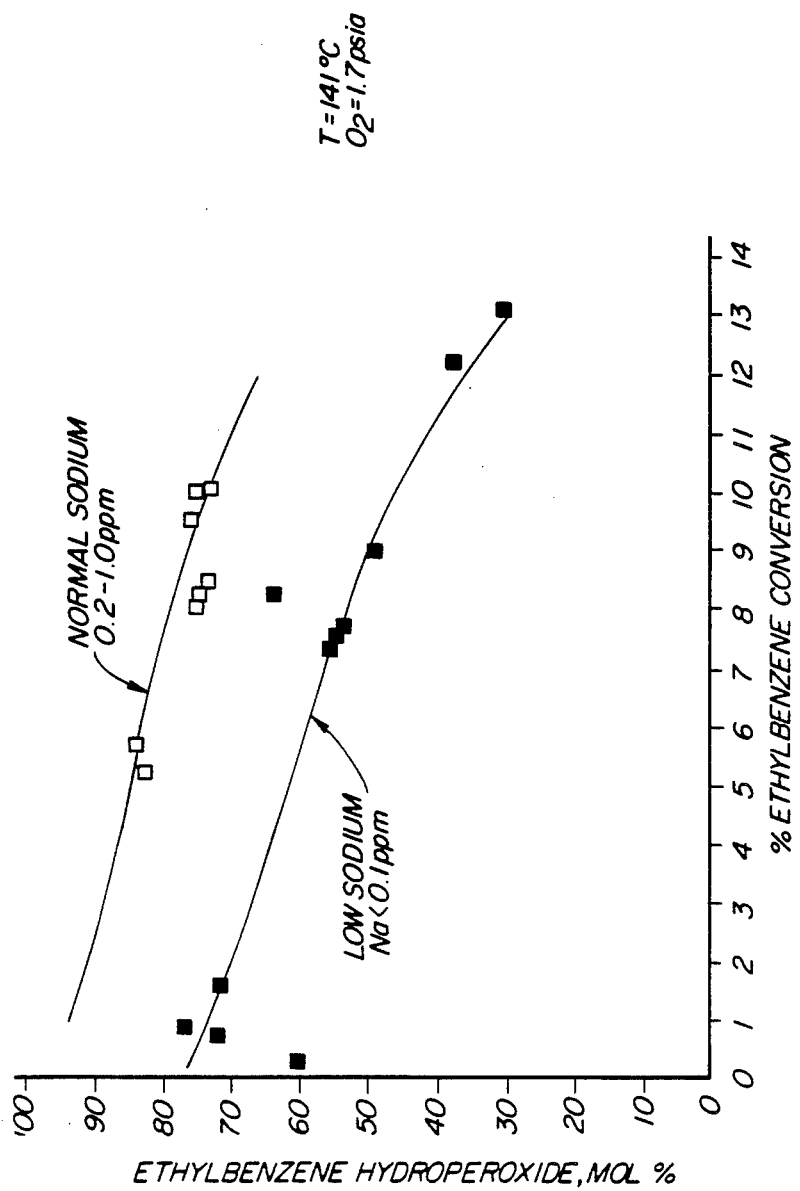
FIG. 3 is a plot of reaction selectivity to ethylbenzene hydroperoxide versus ethylbenzene conversion at various sodium levels.

FIGS. 1 and 2 show the significant impact on acetophenone selectivity in ethylbenzene oxidation by operating at low sodium and high water concentrations in the reactor. Low-sodium concentration is shown to be a necessary and sufficient condition for enhanced acetophenone selectivity, although the effect is increased as water concentration is increased. Water injection has virtually no effect on acetophenone selectivity at sodium levels above 0.2 ppm. At zero water injection, water concentration in the reactor is near 500 ppm resulting from reactions which produce water; at 10% ethylbenzene conversion, acetophenone selectivity is still increased from 14% base-case to about 30%. The increase in acetophenone selectivity occurred completely at the expense of ethylbenzene hydroperoxide selectivity, as shown in FIG. 3.

Figure 4:
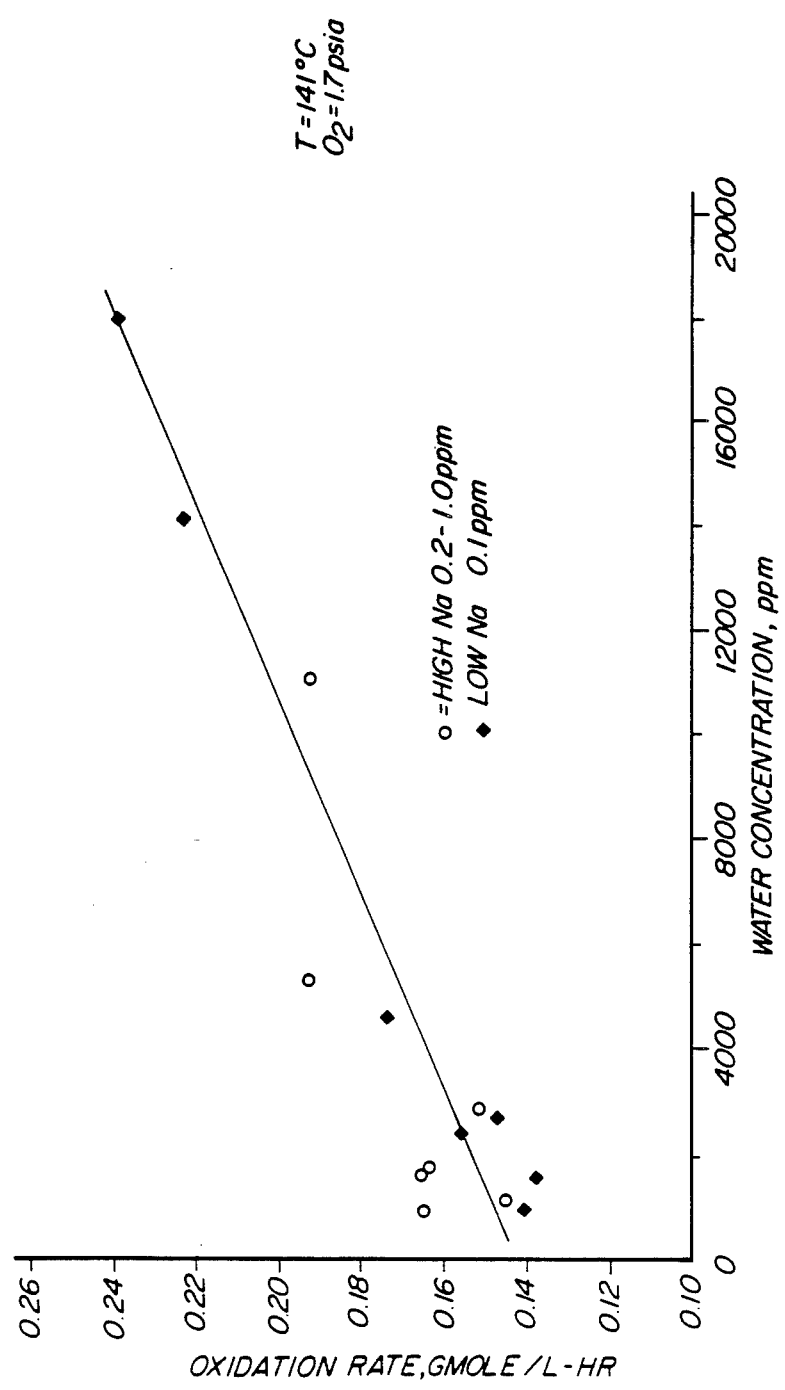
FIG. 4 is a plot of ethylbenzene oxidation rate versus water concentration at normal and low sodium levels.
Figure 5:
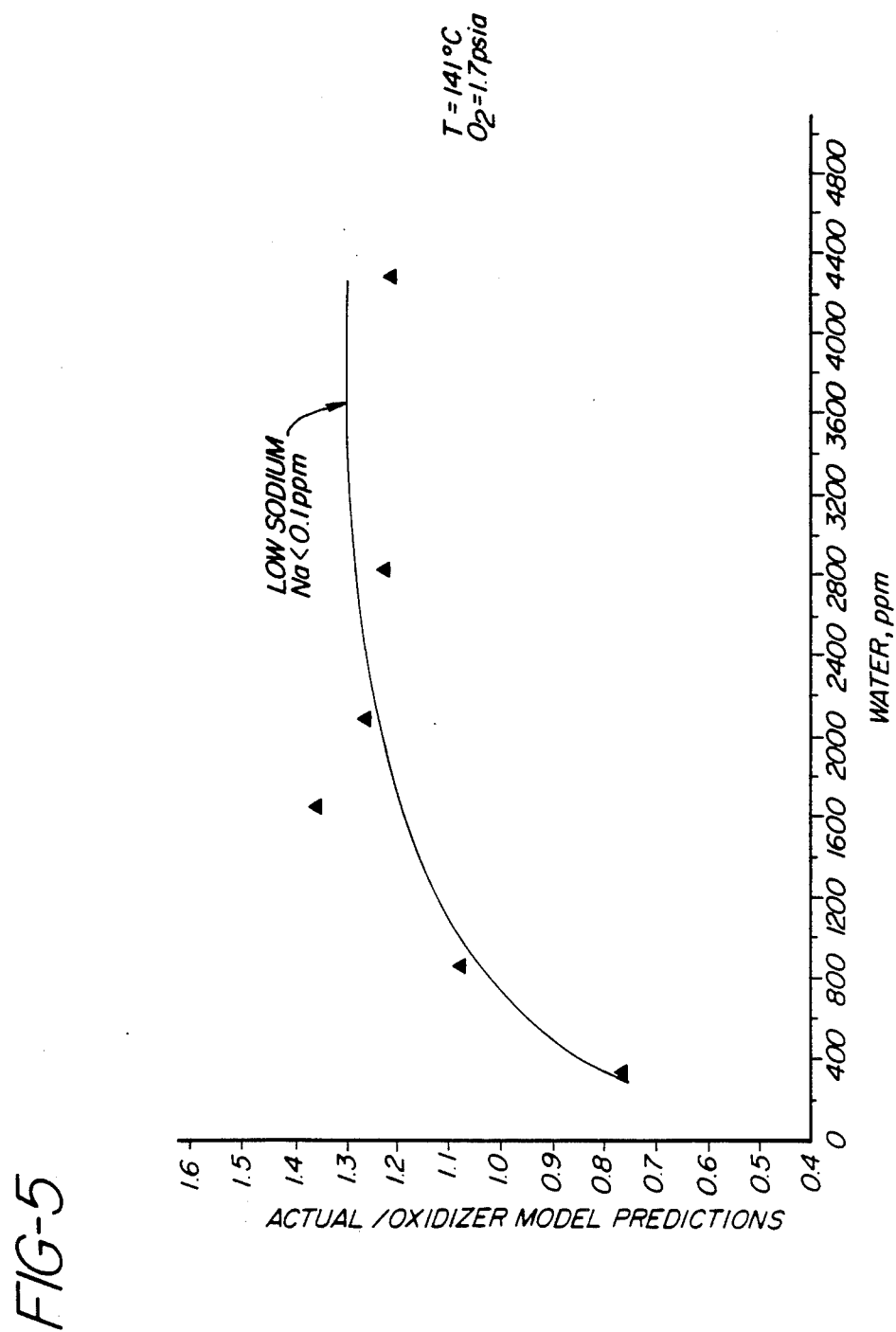
FIG. 5 is a plot of the relative rate of ethylbenzene oxidation versus water concentration at low ethylbenzene conversion levels.

Ethylbenzene oxidation rate was substantially increased by water injection for both high and low sodium cases, as shown in FIG. 4. For the high ethylbenzene conversion cases shown, low water concentration (<2000 ppm) gave slightly lower oxidation rates for low sodium operation than for high sodium operation. At low ethylbenzene conversion (<2%), FIG. 5 shows that this efect is more pronounced; about 600–1200 ppm water at low sodium level is required for the oxidation rate to match base case performance at greater than 2 ppm sodium. Where plural oxidizer zones are employed as shown, for example, in U.S. Pat. No. 4,066,706, water injection to early oxidizer compartments is useful to avoid this drop in oxidation rate.

In order to further illustrate the invention, reference is made to the following examples.

COMPARATIVE EXAMPLE A

Ethylbenzene was continuously oxidized in the single-stage, well-mixed autoclave reactor described above. This example illustrates a base-case of high ethylbenzene conversion (>7%), in which sodium is purposely added to the reactor, but water is not. Thus the oxidation was carried out in accordance with prior procedures designed to maximize the production of ethylbenzene hydroperoxide.

Air was the oxidant, the reaction temperature and pressure were 141° C. and 35 psig, respectively, and oxygen breakthrough in the offgas from the reactor was 5 mol %. By means of a sodium pyrophosphate coating on the reactor surface, a sodium level in the reaction mixture of 2 ppm was maintained. Water fomed during the oxidation was present in amount of 0.11 wt %. Ethylbenzene conversion was 8.36%, with selectivity to ethylbenzene hydroperoxide of 74.5%, to acetophenone of 13.5% and to methyl benzyl alcohol of 7.2%.

EXAMPLE 1

In accordance with the present invention, the high ethylbenzene conversion case illustrated above was modified in order to enhance the production of acetophenone with mimimun disruption of the reaction system. The sodium pyrophosphate coating on the reactor's surface was removed so that no sodium was being continuously added to the reactor during oxidation. Water was not added to the reactor in this example. Otherwise, reaction temperature, pressure, ethylbenzene, feed rate, and offgas oxygen concentration remained the same as in Comparative Example A.

When steady-state operation at the changed conditions was achieved, the sodium content of the reaction mixture was less than 0.1 ppm. Water formed during the oxidation was present in amount of 0.15 wt %. Ethylbenzene conversion was 7.75%, with selectivity of ethylbenzenne hydroperoxide of 52.9%, to acetophenone of 33.1%, and to methyl benzyl alcohol of 8.3%. This example shows that lowering sodium content in the reactor to below 0.1 ppm while maintaining a water content in the range 0.05 to 2.0 wt % is highly effective for shifting product selectivities from ethylbenzene hydroperoxide to acetophenone.

COMPARATIVE EXAMPLE B

This example is provided to demonstrate that water injection into the ethylbenzene oxidation reactor does not cause a substantial shift in product selectivities to acetophenone when sodium concentration is sufficiently high. As in Comparative Example A, a sodium level in the reaction mixture of 2 ppm was maintained by means of a sodium pyrophosphate coating on the reactor surface. By direct water addition to the reactor, a water concentration of 0.52 wt. % was maintained in the reaction mixture. Otherwise, reaction temperature, pressure, ethylbenzene feed rate, and offgas oxygen concentration remained the same as in Comparative Example A.

When stead-state operation was achieved, ethylbenzene conversion was 10.06%, and product selectivities were 74.8% to ethylbenzene hydroperoxide, 15.3% to acetophenone, and 6.3% to methyl benzyl alcohol.

EXAMPLE 2

In accordance with the present invention, another high ethylbenzene conversion case which demonstrates enhanced acetophenone selectivity with minimum disruption of the reaction system was established. In this example, as in Example 1, no sodium was continuously added to the reactor system; sodium in the reaction mixture was less than 0.1 ppm. However, water was continuously added in amount sufficient to provide a water concentration in the reaction mixture of 1.4% by weight. Otherwise, reaction temperature, pressure, ethylbenzene feed rate and offgas oxygen concentration remained the same as in Example A.

When the steady-state operation at the changed conditions was achieved, ethylbenzene conversion was 12.28%, significantly higher than in Comparative Example A and Example 1. Product selectivities were 36.3% to ethylbenzene hydroperoxide, 53.3% to acetophenone, and 7.1% to methyl benzyl alcohol. This example illustrates that at low sodium concentration, water addition increases ethylbenzene conversion and increasees the shift in product selectivities in favor of acetophenone as compared with the lower water concentration in Example 1.

COMPARTIVE EXAMPLE C

This example illustrates a base-case of low ethylbenzene conversion (<2), in which sodium is purposely added to the reactor, but water is not. Thus, the oxidation was carried out in accordance with prior procedures designed to maximize the production of ethylbenzene hydroperoxide. Reaction temperature, pressure, and offgas oxygen concentration remained the same in Example A, but ethylbenzene feed rate was increased in order to lower the liquid residence time in the reactor, and thereby lower the ethylbenzene conversion. As in Comparative Example A, sodium was continuously added to the reaction liquid by means of a sodium pyrophosphate coating on the reactor surface; sodium content of the reaction mixture was 2 ppm.

When stead-state operatin was achieved, ethylbenzene conversion was 1.86%, and water formed during the reaction was present in amount of 0.034 wt. %. Product selectivities were 93.8% to ethylbenzene hydroperoxide, 3.2% to acetophenone, and 2.8% to methyl benzyl alcohol.

EXAMPLE 3

In accordance with the present invention, a low ethylbenzene conversionn case which demonstrates enhanced acetophenone selectivity with minimum disruption of the reaction system was established. In this example, no sodium was continuously added to the reactor system; sodium in the reaction mixture was less than 0.1 ppm. However, water was continuously added in amount sufficient to provide a water concentration in the reaction mixture of 0.28% by weight. Otherwise, reaction temperature, pressure, ethylbenzene feed rate and offgas oxygen concentration remained the same as in Comparative Example C.

When the stead-state operation at the changed conditions was achieved, ethylbenzene conversion was 1.67%. Product selectivites were 71.7% to ethylbenzene hydroperoxide, 19.8% to acetophenone, and 6.6% to methyl benzyl alcohol.

COMPARATIVE EXAMPLE D

The low ethylbenzene conversion case established in Comparative Example C was again modified to attempt to enhance the production of acetophenone with minimum distruption of the reaction system. As in Example 3, the sodium pyrophosphate coating on the reactor's surface was removed so that no sodium was being continuously added to the reactor during oxidation. Water was not added to the reactor in this example. Otherwise, reaction temperature, pressure, ethylbenzene feed rate, and offgas oxygen concentration remained the same as in Comparative Example C and Example 3.

When steady-state operation at the changed conditions was achieved, the sodium content of the reaction mixture was less than 0.1 ppm. Water formed during the oxidation was present in amount of 0.033 wt. %. Ethylbenzene conversion was 0.36%, with selectivity to ethylbenzene hydroperoxide of 60.0%, to acetophenone of 29.9%, and to methyl benzyl alcohol of 4.2%. This example and Example 3 show that lowering sodium content in the reactor to below 0.1 ppm is sufficient for shifting product selectivities in favor of acetophenone, but that without water injection, ethylbenzene conversion, and hence reaction rate is lowered to an unacceptable level. Water injection is shown to be necessary to maintain ethylbenzene oxidation rate at low reactor sodium concentrations and low ethylbenzene conversion conditions.

From the above, the utility of the present invention as a convenient method for substantially enhancing acetophenone production relative to ethylbenzene hydroperoxide production without a substantial disruption of operations will be apparent.

What is claimed is:

1. In a process for the liquid phase molecular oxygen oxidation of ethylbenzene to form products comprised of ethylbenzene hydroperoxide and acetophenone, the ethylbenzene oxidation reaction mixture containing at least 0.2 ppm alkali metal, the method of increasing the amount of acetophenone formed relative to ethylbenzene hydroperoxide which comprises:
   (a) reducing the alkali metal content of the ethylbenzene oxidation reaction mixture to below 0.1 ppm,
   (b) incorporating 0.05 to 2% by weight of water in the ethylbenzene oxidation reaction mixture, and
   (c) thereafter oxidizing ethylbenzene in the said water-containing mixture having said reduced content of alkali metal with molecular oxygen at elevated temperature to form enhanced amounts of acetophenone relative to ethylbenzene hydroperoxide.

2. The process of claim 1 wherein the elevated temperature in step (c) is in the range of about 120°–170° C.

* * * * *